US010281391B2

(12) United States Patent
Kurtz et al.

(10) Patent No.: US 10,281,391 B2
(45) Date of Patent: May 7, 2019

(54) SPECTRALLY PURE SHORT-PULSE LASER

(71) Applicant: Luminit LLC, Torrance, CA (US)

(72) Inventors: Russell Kurtz, Torrance, CA (US); Alkan Gulses, Torrance, CA (US)

(73) Assignee: LUMINIT LLC, Torrance, CA (US)

( * ) Notice: Subject to any disclaimer, the term of this patent is extended or adjusted under 35 U.S.C. 154(b) by 0 days.

(21) Appl. No.: 15/171,499

(22) Filed: Jun. 2, 2016

(65) Prior Publication Data

US 2016/0356706 A1    Dec. 8, 2016

Related U.S. Application Data

(60) Provisional application No. 62/171,825, filed on Jun. 5, 2015.

(51) Int. Cl.
*G01N 21/39* (2006.01)
*G01J 3/10* (2006.01)

(52) U.S. Cl.
CPC ............... *G01N 21/39* (2013.01); *G01J 3/10* (2013.01); *G01N 2021/394* (2013.01)

(58) Field of Classification Search
CPC ........... G01N 21/39; G01N 2021/394; G01N 21/3504; G01N 2021/391; G01N 2201/06113; G01N 2201/0612; G01N 2201/067; G01N 27/44721; G01J 3/10; H01S 3/1623
See application file for complete search history.

(56) References Cited

U.S. PATENT DOCUMENTS

| | | | | |
|---|---|---|---|---|
| 2,907,820 A | * | 10/1959 | Teer | H04N 7/08 348/385.1 |
| 4,174,504 A | * | 11/1979 | Chenausky | H01S 3/1103 372/102 |
| 5,212,711 A | * | 5/1993 | Harvey | H01S 3/06791 372/18 |
| 5,237,331 A | * | 8/1993 | Henderson | G01S 7/4814 342/26 R |
| 5,689,334 A | * | 11/1997 | Atkinson | G01N 21/3504 250/339.13 |
| 5,723,864 A | * | 3/1998 | Atkinson | G01N 21/3504 250/339.13 |
| 5,747,807 A | * | 5/1998 | Atkinson | G01N 21/3504 250/339.13 |

(Continued)

OTHER PUBLICATIONS https://en.wikipedia.org/wiki/Pockels_effect.*
https://en.wikipedia.org/wiki/Fabry%E2%80%93P%C3%A9rot_interferometer.*
https://www.astro.cf.ac.uk/observatory/solarobservatory/equipment/?page=fabryperot.*

*Primary Examiner* — Mohamed K Amara
(74) *Attorney, Agent, or Firm* — Husch Blackwell LLP

(57) ABSTRACT

A laser system containing an etalon to reduce the spectral bandwidth and for tuning, with cavity dumping to generate the short pulses is described. The resulting system is stable and not overly complicated. The combination of cavity dumping with an intracavity etalon enables the invention to produce a string of short pulses, each of which has a very narrow spectral bandwidth. Tuning the wavelength over a spectral range that is very small, but much larger than the laser's spectral bandwidth, enables the invention to use dual-wavelength lidar, DIAL, differential spectroscopy, or a combination of these methods to measure the concentration of the desired chemicals with excellent accuracy.

15 Claims, 2 Drawing Sheets

(56) References Cited

U.S. PATENT DOCUMENTS

Figure 1:
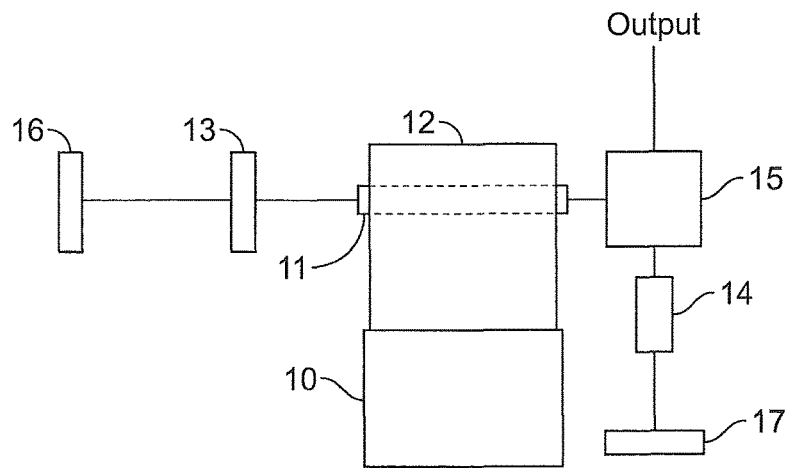

| | | | | |
|---|---|---|---|---|
| 5,761,227 A * | 6/1998 | Hargis | ............... | H01S 3/042 |
| | | | | 372/22 |
| 5,841,533 A * | 11/1998 | Atkinson | ......... | G01N 21/3504 |
| | | | | 250/339.1 |
| 5,917,188 A * | 6/1999 | Atkinson | ......... | G01N 21/3504 |
| | | | | 250/339.13 |
| 5,991,032 A * | 11/1999 | Atkinson | ............ | G01N 21/39 |
| | | | | 250/339.13 |
| 5,999,259 A * | 12/1999 | Atkinson | ............ | G01N 21/39 |
| | | | | 250/339.13 |
| 7,519,096 B2 * | 4/2009 | Bouma | ............. | A61B 5/0059 |
| | | | | 372/102 |
| 7,800,753 B1 * | 9/2010 | Hug | ..................... | G01J 3/10 |
| | | | | 356/301 |
| 7,949,019 B2 * | 5/2011 | Bouma | ............... | G01J 3/02 |
| | | | | 372/102 |
| 9,176,319 B2 * | 11/2015 | Bouma | ............... | G01J 3/02 |
| 9,178,330 B2 * | 11/2015 | Oh | ................. | H01S 3/08009 |
| 2002/0018288 A1 * | 2/2002 | Rieger | ............. | H01S 3/0606 |
| | | | | 359/342 |
| 2005/0207943 A1 * | 9/2005 | Puzey | ................. | C12Q 1/04 |
| | | | | 422/82.05 |
| 2006/0262815 A1 * | 11/2006 | Klimov | ............ | H01S 3/09415 |
| | | | | 372/18 |
| 2009/0122816 A1 * | 5/2009 | Wagner | ............. | H01S 3/1068 |
| | | | | 372/20 |
| 2013/0062514 A1 * | 3/2013 | Csutak | ............. | G01J 3/0256 |
| | | | | 250/262 |
| 2015/0139451 A1 * | 5/2015 | Fischer | ............. | G01D 5/266 |
| | | | | 381/111 |
| 2017/0365974 A1 * | 12/2017 | Kurtz | ............... | H01S 3/1062 |

* cited by examiner

SPECTRALLY PURE SHORT-PULSE LASER

FIELD OF THE INVENTION

This invention is in the field of optical spectroscopy, and particularly laser absorption spectroscopy.

BACKGROUND OF THE INVENTION

Laser absorption spectroscopy is a common method of measuring and identifying chemicals. For example, light from an Er:YAG laser operating at a wavelength near 1645 nm is strongly absorbed by methane; the reduction in laser intensity, due to absorption, can be used to calculate the amount of methane probed by the laser beam. The laser source is more effective if its spectral bandwidth is limited; a spectrally pure laser is more useful than one that is not as pure. In addition, it is often easier to measure the absorption signal in a string of short pulses instead of in a long pulse or a continuous laser. A stable, spectrally pure laser output with a high repetition rate of short pulses is ideal. There can be a tradeoff between short pulses and spectral purity.

There are many applications for high-quality laser absorption spectroscopy. The methane absorption at 1645 nm is already used by Er:YAG lidar systems to measure methane concentration in air. Likewise, the carbon dioxide absorption near 2100 nm has been used by Ho:YAG lidar systems to measure carbon dioxide concentration in the air. Laser absorption spectroscopy is also used to measure, for example, pollutants dissolved in water.

Due to the effects of climate change, there is an increasing need to measure greenhouse gases accurately. These include carbon dioxide, methane, nitrous oxide, ozone, and chlorofluorocarbons. Monitoring these gases, and finding sources of leaks of the gases, is a key application of laser absorption spectroscopy. As one example, a laser mounted in an aircraft and pointed to the ground can be used as the source; the reflected signal, which can then be captured by a measurement system mounted on the same aircraft, passes through a column of atmosphere twice, creating a long absorption path that can enhance absorption of the laser beam and increase measurement accuracy.

There are several laser absorption spectroscopy systems under development to measure greenhouse gases, atmospheric pollutants, and chemicals dissolved in the oceans. Most such systems can only measure a single chemical, although some, such as those that use an optical parametric oscillator, can be tuned enough to potentially measure more than one chemical. The shortest laser pulses typically used for these measurements is 7-10 ns, and the spectral bandwidth of the laser is typically larger than a single absorption feature.

CONCISE DESCRIPTION OF THE DRAWINGS

Figure 2:
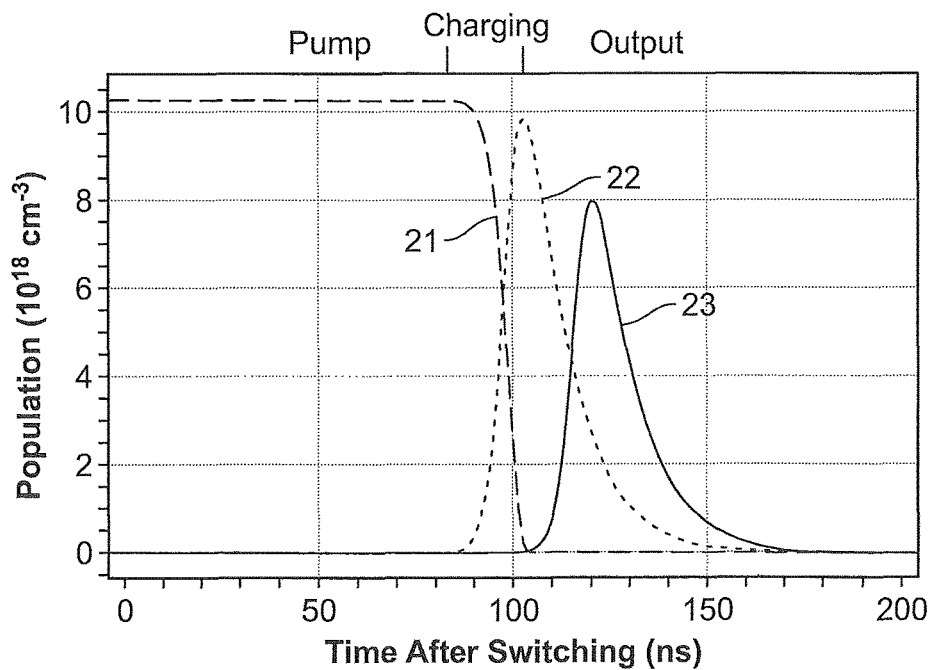
Figure 3:
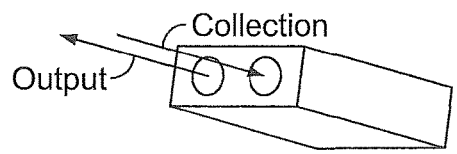
Figure 4:
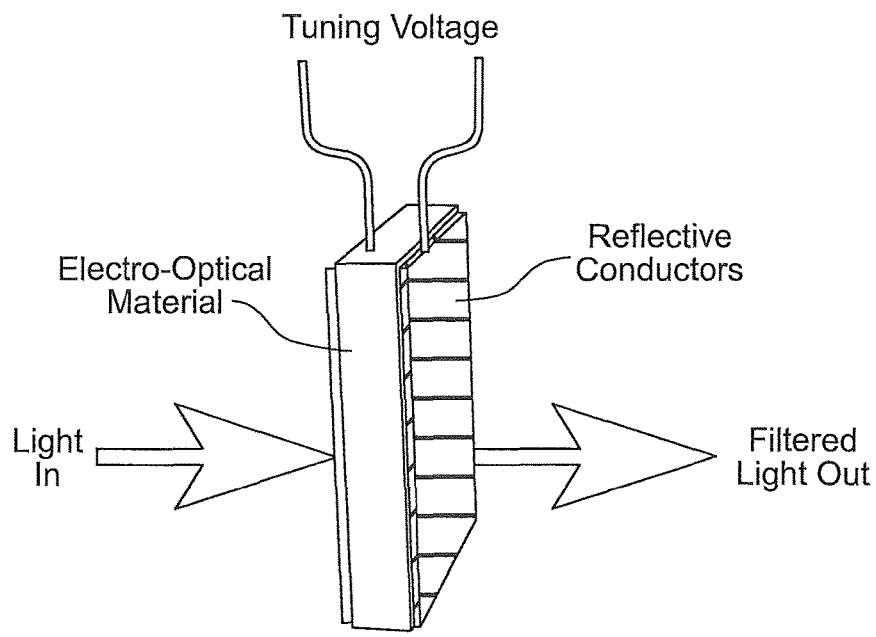
Figure 5:
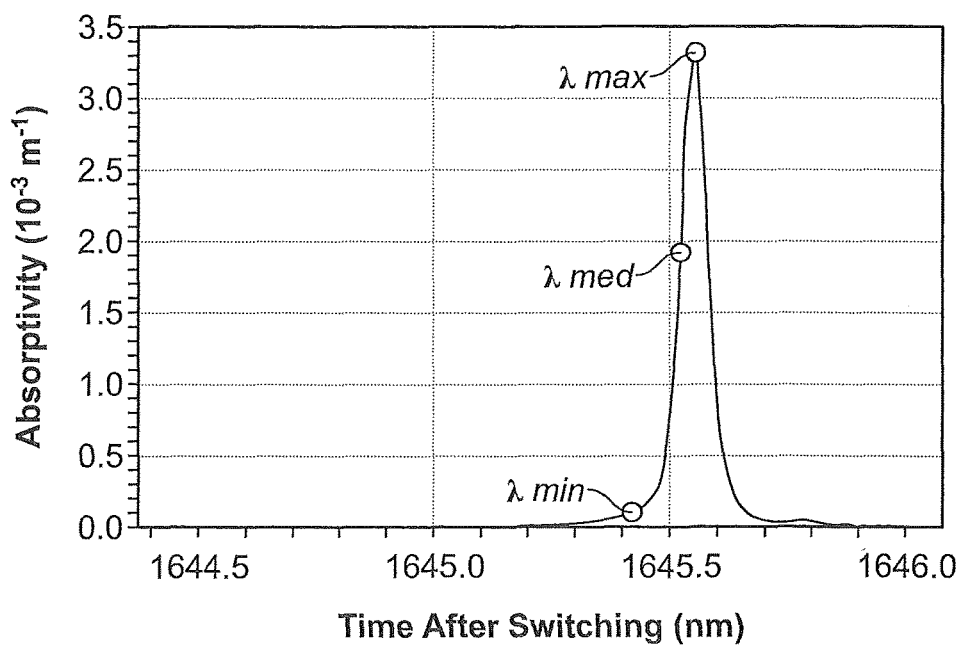

FIG. 1 is a schematic of the laser apparatus
FIG. 2 is a graph of energy transfer within the laser material
FIG. 3 shows the laser absorption spectroscopy system
FIG. 4 is the layout of a tunable etalon
FIG. 5 shows an absorption feature (in this case, methane) and the three wavelengths used for laser absorption spectroscopy and differential spectroscopy.

SUMMARY OF THE INVENTION

To address the need for a spectroscopy laser that produces short pulses but is also spectrally pure, a laser system containing an etalon to reduce the spectral bandwidth and for tuning, with cavity dumping to generate the short pulses is described. The resulting system is stable and not overly complicated. The combination of cavity dumping with an intracavity etalon enables the invention to produce a string of short pulses, each of which has a very narrow spectral bandwidth. Tuning the wavelength over a spectral range that is very small, but much larger than the laser's spectral bandwidth, enables the invention to use dual-wavelength lidar, DIAL, differential spectroscopy, or a combination of these methods to measure the concentration of the desired chemicals with excellent accuracy. Use of cavity dumping, rather than Q-switching, to produce short pulses enables the laser to combine spectral purity with short pulse length, because the light in a cavity-dumped pulse has passed through the etalon dozens of times, while the light in a Q-switched pulse might only pass through an etalon once or twice.

DETAILED DESCRIPTION OF THE INVENTION

The laser apparatus 30 of the subject invention comprises four subsystems in FIG. 2: pump and power (10), laser (11, 12, 16, 17), spectral (13), and pulse forming (14, 15). Subsystem 10 takes electrical power—from a battery, wall plug, or other electric supply—and first converts it as needed by the system, then uses it to drive semiconductor pump lasers. The laser may be formed of a laser material such as crystal, glass, ceramic or other solid state material and be Er:YAG, Ho:YAG, Tm:YAG, Nd:YAG, Cu vapor, HF, CO2, or other material system, dependent on the compound being detected. This subsystem includes the power to drive the Pockels cell (14) in the subsystem (14, 15), the tunable etalon (13) in Subsystem (13), and whatever temperature control is needed. Subsystem (11, 12, 16, 17) is the main laser portion, including the pump cavity (12), rod (11), and mirrors (16, 17). It takes the pump light and converts it into a highly coherent beam at the desired wavelength. Subsystem (14, 15), comprising the Pockels cell (14) and the polarizer (15), is the pulse forming subsystem.

The Heisenberg Uncertainty Principle describes the tradeoff between bandwidth and pulse length. In particular, it defines the minimum value of either one, if the other is known. It is usually described by the relationship $$\Delta v \times \Delta \tau > 1/2\pi,$$

where $\Delta v$ is the spectral bandwidth and $\Delta \tau$ is the pulse length. This is the absolute limit; to produce a pulse whose length is shorter than $t_p$ requires a bandwidth $>1/2\pi t_p$. No real laser can meet the minimum limit; few lasers can even reach the level $$\Delta v = 1/\Delta \tau.$$

As an example, a laser whose pulse length is 10 ns will almost never have a spectral bandwidth less than 100 MHz. Use of cavity dumping with an intracavity etalon, however, enables a closer approach to the absolute limit of 16 MHz. The subject invention can produce a pulse 6 ns long, with a spectral bandwidth of 50 MHz, twice the absolute limit and more than a factor of 3 better than the "transform limit" defined by the inverse of the pulse length.

In one embodiment, as shown in FIG. 1, a laser rod (11) could be placed in a cavity (12), enabling side-pumping by the pump lasers (10) with equal or better efficiency than the traditional end-pumping. Such a cavity reduces pump beam quality requirements. The laser rod, then excited, could store the pump energy in the laser inversion (FIG. 2, 21), in which ions are excited into energy levels above the ground level, and trapped in an excited state for some time. In this portion of operation, the pump portion, the pulse forming system (14, 15) is preventing lasing by reflecting fluorescence from the laser rod out of the cavity, keeping the potential laser light from being captured by both mirrors (16, 17), although it still reflects from one of them (16). After a sufficient amount of time that enables the inversion to be significantly greater than would normally be achievable in laser operation, the pulse forming system can be switched to pass the oscillating light (FIG. 2, 22), which is then fully contained by the two mirrors. During this portion of operation, the charging portion, energy is moved from the inversion into the oscillating photon stream. Some time later, the oscillating light (FIG. 2, 23) can be dumped out of the cavity when the pulse forming system is switched back into the mode in which any light in the cavity is reflected out. This is the output portion of operation, and the light coming out is the laser output. The optimum length of the charging portion can be calculated by rate equation analysis. In this embodiment, the intracavity etalon (FIG. 1, 13), which reduces the spectral bandwidth of the laser output, can be adjusted to tune the output wavelength, preferably by means of changing the distance between the two reflecting surfaces that form the etalon. Since the etalon is always in the cavity, it controls the laser output spectrum; during the charging portion of operation, the etalon can reduce the spectral bandwidth of light inside the cavity to be extremely narrow, even potentially as narrow as is limited by the Heisenberg Uncertainty Principle. In this embodiment, the etalon can tune three successive laser pulses such that one is tuned to the peak wavelength of a chemical absorption feature for maximum absorption, one is tuned to maximum transmission, and one is tuned to a value at which the chemical has a medium absorption value that is somewhat less than the maximum. The laser can also have available a known sample of the chemical being measured, enabling frequent, or even simultaneous, calibration of the output wavelengths. The returned intensity at the minimum absorption wavelength can be used to normalize the measurement, since the measurement at the minimum absorption wavelength is a measurement of loss in the laser propagation when there is no absorption but only other losses. After normalization, the remaining two measurements can be used differentially to approximate the slope of the absorption curve as a function of wavelength. This calculation, the differential of received intensity with respect to wavelength, is defined as $$\frac{dI}{d\lambda} \approx \frac{I_{max} - I_{med}}{\lambda_{max} - \lambda_{med}}.$$

In this equation, $I_{max}$ is the normalized intensity received at the wavelength of maximum absorption, $I_{med}$ is the normalized intensity received at the wavelength of medium absorption, $\lambda_{max}$ is the wavelength of maximum absorption, and $\lambda_{med}$ the wavelength of medium absorption. This calculated value is used to calculate differential absorption. Combining differential absorption with normalized direct absorption measurements can increase the accuracy of chemical recognition and measurement. The differential absorption value is more sensitive than a simple absorption measurement, and the normalized intensity measurements are affected only by the absorbing material, the amount of this material in the laser path length, and the path length itself.

The invention, thus comprises a laser absorption spectroscopy system, with a laser, including the laser material, a means of energizing the laser material, at least two high-reflectivity mirrors, a pulse forming system that enables switching between containing light within the cavity and directing light out of the cavity, and a tunable etalon; it also includes a receiver, comprising at least one photodetector that is sensitive at the laser wavelength, and with a digital output, a means of energizing this photodetector, collection optics, and a means of calculating ratios of photodetector measurements, such as with a computer. The laser material may be solid-state such as crystal, glass, ceramic, other solid-state method or a combination of these materials. The energizing means may be optical such as one or more pump lasers, one or more pump diodes, one or more flashlamps, or other optical pumping method. Further, the energizing means may be electrical, chemical or magnetic. The collection optics may include at least one lens, and at least one mirror. The pulse forming system may have a Pockels cell, its driver, and a polarizer. The etalon tuning may be accomplished by applying an electric or magnetic field. Further, the means of energizing the laser material may use side-pumping and each laser material is not affected by pumping the other material; calibration of the output wavelengths may be real time.

Also, the spectroscopic laser apparatus of the subject invention may include an ionic laser material in a crystalline host, where the laser material is side-pumped by semiconductor lasers and the output is cavity dumped through the use of a Pockels cell and a polarizer; a tunable etalon may be included to select specific wavelengths which are selected to normalize the measurement and/or to enable the use of differential spectroscopy; the laser output can be tuned to a region wherein the chemical being analyzed has known absorption features.

It will be understood that the foregoing description is of preferred exemplary embodiments of the invention and that the invention is not limited to the specific forms shown or described herein. Various modifications may be made in the design, arrangement, and type of elements disclosed herein, as well as the steps of making and using the invention without departing from the scope of the invention as expressed in the appended claims.

What is claimed is:

1. A laser absorption spectroscopy system, comprising: laser material, a pump laser, at least two high-reflectivity mirrors, a pulse forming system that enables switching between containing light within a cavity and directing light out of the cavity in three successive pulses via cavity dumping, and one etalon within the cavity turned to three predetermined wavelengths;

wherein
a first pulse is tuned to a first wavelength comprising a peak absorption wavelength of a chemical being analyzed,
a second pulse is tuned to a second wavelength comprising a maximum transmission wavelength of the chemical, and
a third pulse is tuned to a third wavelength comprising a medium absorption wavelength of the chemical;

a receiver, comprising at least one photodetector that is sensitive to each of the three predetermined wavelengths, collection optics; and a computer for calculating ratios of photodetector measurements.

2. The system of claim 1, wherein the laser material is solid-state.

3. The system of claim 1, wherein the pump laser is optical.

4. The system of claim 1, wherein the pump laser is electrical or magnetic.

5. The system of claim 1, wherein the pump laser is chemical.

6. The system of claim 1, wherein the collection optics include at least one lens.

7. The system of claim 1, wherein the collection optics include at least one mirror.

8. The system of claim 1, wherein the pulse forming system comprises a Pockels cell, a driver, and a polarizer.

9. The system of claim 1, wherein an output of the photodetector is digitized.

10. The system of claim 1, wherein the etalon tuning is accomplished by applying an electric or magnetic field.

11. The system of claim 1, wherein the pump laser uses more than one laser material.

12. The system of claim 11, wherein the laser materials used are different from each other.

13. The system of claim 11 wherein the more than one laser material is not affected by pumping the other material.

14. The system of claim 1, wherein the pump laser uses side-pumping.

15. A spectroscopic laser apparatus for determining the identity and concentration of a substance, comprising:
   an ionic laser material in a crystalline host;
   the laser material being side-pumped by semiconductor lasers;
   the output is dumped out of a cavity through the use of a Pockels cell and a polarizer;
   wherein the output comprises three successive pulses; each pulse tuned by one etalon within the cavity to select and output light of three predetermined wavelengths; wherein the predetermined wavelengths are tuned by changing the distance between a first and a second reflecting surface of the etalon, the successive pulses tuned to:
   A first pulse having a first wavelength tuned to a peak absorption wavelength of a chemical being analyzed,
   A second pulse having a second wavelength tuned to a maximum transmission wavelength of the chemical, and
   A third pulse having a third wavelength tuned to a medium absorption wavelength of the chemical.

* * * * *